United States Patent [19]

Patil et al.

[11] Patent Number: 5,574,183

[45] Date of Patent: Nov. 12, 1996

[54] PREPARATION OF OPTICALLY ACTIVE ALIPHATIC CARBOXYLIC ACIDS

[75] Inventors: Deepak R. Patil, Orangeburg, S.C.; Venkataraman Ramachandran, Baton Rouge, La.

[73] Assignee: Albemarle Corporation, Richmond, Va.

[21] Appl. No.: 378,049

[22] Filed: Jan. 24, 1995

[51] Int. Cl.$^6$ ................................................. C07B 55/00
[52] U.S. Cl. ................................................. 562/401
[58] Field of Search ............................................ 562/401

[56] References Cited

U.S. PATENT DOCUMENTS 4,246,193  1/1981  Holton ................................ 260/501.17
4,625,054  11/1986  Bernini ................................ 562/401
5,380,927  1/1995  Paradies ................................ 562/493

Primary Examiner—Paul J. Killos
Attorney, Agent, or Firm—Philip M. Pippenger

[57] ABSTRACT

A process for the separation of a racemic mixture of certain aliphatic carboxylic acids or esters thereof is disclosed. The process comprises i) forming a diastereomeric salt by reaction comprising said racemic mixture of a $C_1$ to $C_6$ linear or branched aliphatic carboxylic acid and an amount of a chiral organic base sufficient to react with one of the enantiomers of the racemic mixture; ii) precipitating from the reaction solution formed in step i) the diastereomeric salt; iii) separating said precipitated diastereomeric salt; iv) decomposing the salt into its enantiomeric component and its organic base component; and v) isolating a substantially pure enantiomer from said decomposed salt.

6 Claims, No Drawings

PREPARATION OF OPTICALLY ACTIVE ALIPHATIC CARBOXYLIC ACIDS

This invention relates to the preparation of optically active carboxylic acids and the esters thereof. More particularly this invention relates to the preparation of aliphatic carboxylic acids and the esters thereof by first forming the diasteromeric salts of such materials and then separating the diasteromeric salts.

Resolution of racemic aryl-substituted aliphatic carboxylic acids has been described in the literature. Kaiser et al, J. Pharm. Sci., Vol. 65, No. 2, 269–273 (February 1976) formed the S(−) α-methylbenzylamine salt of S(+)-ibuprofen, removed it from the reaction mixture by filtration, and recrystallized it from isopropanol and then from methanol. After acidifying with 3N aqueous sulfuric acid, and extracting with ether, S(+)-ibuprofen was obtained, m.p. 50°–52° C., $[\alpha]_D$+57., with 95% optical purity as determined by GLC analysis. Cox et al, J. Pharmacol. Exp. Ther., Vol. 232, No. 3, 636–643 (March 1985), using Kaiser et al's method, were able to obtain an S(+)-ibuprofen preparation which was 99% S isomer and 1% R isomer (w/w).

U.S. Pat. No. 4,246,164 describes a process for resolving (±)-6-methoxy-α-methyl-2-naphthylacetic acid into its enantiomers by reacting the racemic mixture with N-methyl-D-glucamine to produce the corresponding diastereomeric N-methyl-D-glucamine salt pan. Because of the very different solubilities of these salt pans, separation is facilitated.

Other methods of separating the enantiomers of racemates can be effected by preparing a salt of the acid with an alkaloid or similar resolving agent such as cinchonidine, then separating the products by fractional crystallization from a solvent in which the salt of the dextrorotatory isomer is least soluble. The (+)-salt can then be acid cleaved to yield pure enantiomer. See for example, U.S. Pat. No. 4,209,638 issued Jun. 24, 1980, and Alvarez U.S. Pat. No. 3,637,767 issued Jan. 25, 1972, which relates to resolution of naproxen and related compounds.

According to the present invention, there is provided a process for increasing the amount of the desired enantiomer obtained from a racemic mixture of $C_1$ to $C_6$ linear or branched aliphatic carboxylic acid or ester thereof. The process comprises first forming a diastereomeric salt of one of the enantiomers of the racemic mixture of the $C_1$ to $C_6$ linear or branched aliphatic carboxylic acid or ester thereof by reacting a solution of the racemic mixture with an amount of an N-alkyl-D-glucamine that is sufficient to preferentially combine with one of the enantiomers of the racemic mixture but not the other; precipitating the diastereomeric salt from the solution followed by separation of the salt. The separated salt is then decomposed into its constituent parts, i.e. into (a) the enantiomer of the $C_1$ to $C_6$ linear or branched aliphatic carboxylic acid or ester thereof and (b) N-alkyl-D-glucamine. The enantiomer is obtained (isolated) as a substantially pure crystalline product. The mother liquor remaining after separation of the diastereomeric salt comprises the solvent and the other unreacted enantiomer. It can be separated from the solvent and isolated in substantially pure form.

The $C_1$ to $C_2$ linear or branched aliphatic carboxylic acids and esters useful in the process of the present invention have the formula $$R_4-\underset{\underset{R_2}{|}}{\overset{\overset{R_3}{|}}{C}}-\overset{O}{\overset{\|}{C}}-OR_1 \qquad I$$

where $R_1$ is hydrogen or $C_1$ to $C_6$ linear or branched alkyl, $R_2$, $R_3$ and $R_4$ are different and are hydrogen or $C_1$ to $C_6$ linear or branched alkyl, e.g., methyl or ethyl; aralkyl, e.g., benzyl; cycloalkyl, e.g., cyclopropyl, cyclobutyl, cyclopentyl, cyclohexyl; alkyl-substituted cycloalkyl, e.g., methylcyclohexyl; $C_6$ to $C_{10}$ aryl, e.g., phenyl unsubstituted or substituted with for example, methyl, dimethyl, butyl especially isobutyl or phenyl substituted with $C_1$ to $C_4$ alkylthio, $C_1$ to $C_4$ alkoxy, benzoyl, cyano or halo, e.g., fluoro or chloro; $C_1$ to $C_6$ linear or branched aryloxy, e.g., phenoxy or phenoxy substituted with for example, methyl, dimethyl, butyl or isobutyl or phenoxy substituted with $C_1$ to $C_4$ alkylthio, $C_1$ to $C_4$ alkoxy, cyano or halo; $C_1$ to $C_6$ alkylthio, e.g., methylthio; $C_2$ to $C_8$ cycloalkenyl, e.g., cyclohexenyl; trifluoromethyl; halo, e.g., fluoro or chloro.; $C_4$ to $C_5$ heteroaryl, e.g., furyl, pyrrolyl, thienyl; or $C_{10}$ to $C_{14}$ aryl, e.g., naphthyl or naphthyl substituted with $C_1$ to $C_4$ alkyl, e.g., methyl; $C_1$ to $C_4$ alkoxy, e.g., methoxy or ethoxy, halo; or biphenyl unsubstituted or substituted with methyl or halo, especially fluoro. Preferred compounds of formula I are those of the formula

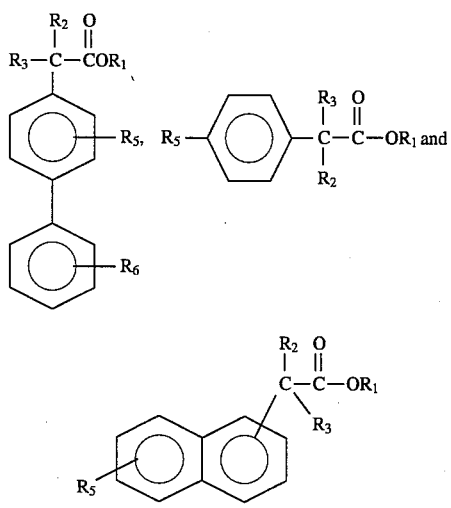

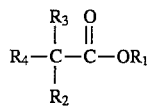

where $R_1$, $R_2$ and $R_3$ are as previously defined and $R_5$ and $R_6$ are $C_1$ to $C_4$ linear or branched alkyl $C_1$ to $C_4$ linear or branched alkoxy or halo.

The process of the present invention is particularly applicable to 2-(3-benzoylphenyl)propionic acid, 6-methoxy-α-methyl-2-naphthylacetic acid and to 2-(4-isobutylphenyl) propionic acid and especially in obtaining a preponderance of the S(+) isomer of these compounds.

The invention is carried out by using a racemic mixture (a mixture of both the (+) and (−) or dextro and levo rotorary forms) or a mixture containing a preponderance of one of the enantiomers of these carboxylic acids. The use of racemic mixtures is preferred. However, it should be understood that in this step, the process itself does not convert one form of the stereoisomers to the other form but only separates such forms. Further, because the separation of isomers gives rise to a soluble product largely containing one enantiomer and an insoluble product largely containing the other enantiomer as the enantiomeric salt, a high purity material is obtained that requires a minimum number of recrystallizations (usually not more than two) to give a product with exceptional high optical purity.

The precipitated salt obtained from the process of the present invention is further treated to produce the free aliphatic carboxylic acid thereof by using any conventional means. For example, hydrolysis of the salt with a dilute mineral acid and extraction with a suitable organic solvent produces the purified aliphatic carboxylic acid. Further extraction and recrystallization with a suitable solvent can increase the purity to even a greater extent.

The first step in the reaction sequence for the separation of the racemic mixtures used in the present invention is to form a salt solution of the aliphatic carboxylic acid with a chiral organic base.

The organic base is preferably an aliphatic, aromatic or mixed aliphatic and aromatic amine. Preferred chiral organic bases are the trisubstituted $C_1$ to $C_6$ linear or branched alkyl amines and the trisubstituted mixed $C_1$ to $C_6$ linear or branched alkyl, $C_6$ to $C_{10}$ arylamines such as methylbenzylamine and the like. However, the most preferred chiral organic base is one that is an N-alkyl-D-glucamine where alkyl is $C_6$ to $C_{12}$ linear or branched alkyl, e.g., methyl, ethyl, n-propyl, i-propyl, n-butyl, i-butyl, t-butyl, n-pentyl, n-hexyl, n-octyl, n-dodecyl, etc. An especially preferred organic base is N-methyl-D-glucamine. Where such chiral organic base is used in this first step, then the solvent employed to form the salt solution is preferably a liquid, inert, organic one. Most preferably such solvents include the ketone solvents or the aliphatic hydrocarbon solvents, i.e., $C_4$ to $C_{14}$ hydrocarbons. Particularly preferred is acetone, hexane or octane as such solvent.

The amount of chiral organic base added to the racemic solution is critical to the success of the process of this invention. It has been discovered that these organic bases preferentially react with one of the enantiomers of the racemic mixture over the other. Therefore, assuming that the racemic mixture to be resolved by the process of the present invention is, in fact, a 50:50 mixture of (+) and (−) enantiomeric forms, then only sufficient base should be added to react with one of the forms, i.e., for 1 mol of a 50:50 racemic mixture, 0.5 mol of organic base should be added to the solution. The base complexes with one enantiomer to form a salt. The other enantiomer does not react to any great extent. A preferred amount of base is 0.25 mol based on one mole of the racemic mixture. While lesser amounts of base may be used, i.e., 0.1 mol based on one 1 mol of racemic mixture, no economic advantage accrues.

It should be noted that this separation may be carried out in the presence of a chiral inorganic or organic base such as described in U.S. Pat. No. 5,235,095, incorporated herein by reference. At this point in the reaction sequence (during the admixture of the organic base and the aliphatic carboxylic acid or ester), the salt solution may be heated, e.g., to a temperature of 25° C. to 125° C., preferably 75° C. to 120° C. or the heating can occur after the salt solution is formed and before any further separation is effected. Heating is typically carried out from 1 to 116 hours, preferably from 2 to 8 hours.

As noted above, the addition of the organic amine to the racemic mixture results in a reaction mass comprising the salt formed from the organic amine and the reactive enantiomer, the unreacted enantiomer and the solvent. In the most preferred embodiment of the present invention, this salt is the N-methyl-D-glucamine salt of S(+)-6-methoxy-α-methylnaphthylacetic acid or of 2-(4'-isobutylphenyl)propionic acid. The salts are crystalline solids in the preferred solvents and precipitate readily from solution. Thereafter, the salts are easily separated by conventional techniques, e.g., centrifugation, filtration, etc.

It should be noted that the process of the present invention is particularly adapted to the economical conversion of racemic mixtures to the diastereomeric S-(+)-salt and then, ultimately to the free enantiomer. (Of course, the R-salt may be the most reactive one, in which case the following discussion should be applied in reverse.) The method of the present invention essentially provides a solid precipitate enriched in the S-enantiomeric salt and a liquid filtrate enriched in the R- or (−)-enantiomer. Liberation of the desired S-enantiomer from the precipitated salt is readily accomplished by for example, acidification of the salt with for example, dilute mineral acid or any other inorganic or organic acid conventionally known to hydrolyze salts of this nature. While this procedure leaves the filtrate as an undesired by-product, it can be further treated with acid or base to convert the R-enriched filtrate to the racemic mixture. This mixture can then be reused in the process of the present invention, using the organic base recovered from the above conversion step. Thus, the process of the present invention lends itself readily to a recycling-type of procedure.

The invention is illustrated by the following Examples.

EXAMPLE 1

| Naproxen(DL) | 10 gms |
| N-Methyl-D-glucamine | 2.12 gms |
| Triethylamine | 3.3 gms |
| Acetone | 125 ml |

Stirred a mixture of naproxen(DL), N-methyl-D-glucamine, triethylamine in acetone for 72 hours. The slurry was filtered, washed with acetone, and dried under vacuum. The solid obtained (naproxen-N-methyl-D-glucamine salt) was weighed and analyzed for S(+)-naproxen content.

| Total Weight of Dried Sample | 3.7 gms |
| Theoretical Weight of Salt | 4.48 gms |
| % Recovery | 82.6 |
| Optical Purity = | 97.4% S; 2.6% R |

EXAMPLE 2

| Naproxen(DL) | 10 gms |
| N-Methyl-D-glucamine | 2.12 gms |
| Triethylamine | 0.0 gms |
| Acetone | 125 ml |

Stirred a mixture of naproxen(DL), N-methyl-D-glucamine, in acetone for 72 hours. The slurry was filtered, washed with acetone and dried under vacuum. The solid obtained (naproxen-N-methyl-D-glucamine salt) was weighed and analyzed for S(+)-naproxen content.

| Total Weight of Dried Sample | 4.36 gms |
| Theoretical Weight of Salt | 4.48 gms |
| % Recovery | 97.3 |
| Optical Purity = | 97.4% S; 2.6% R |

EXAMPLE 3

| Naproxen(DL) | 10 gms |
| N-Methyl-D-glucamine | 2.12 gms |
| Triethylamine | 0.0 gms |
| Acetone | 125 ml |

Stirred a mixture of naproxen(DL), N-methyl-D-glucamine, in acetone for about 117 hours. The slurry was filtered, washed with acetone and dried under vacuum. The solid obtained (naproxen-N-methyl-D-glucamine salt) was weighed and analyzed for S(+)-naproxen content.

| Total Weight of Dried Sample | 4.57 gms |
| Theoretical Weight of Salt | 4.48 gms |
| % Recovery | >100 |
| Optical Purity = | 97.7% S; 2.3% R |

Naproxen salt sample was dissolved in 50 ml water neutralized with 1N HCl to pH ~2 and extracted with diethylether. Ether layer was dried and evaporated to give 2.24 gms of naproxen.

| Optical Purity = | 97.8% S; 2.2% R |

We claim:

1. A process for separating the enantiomers of a racemic mixture of an aryl-substituted $C_1$–$C_6$ aliphatic carboxylic acid or ester thereof which comprises (A) reacting about 0.1–0.25 molar proportion of an N-alkyl-D-glucamine with a solution of one molar proportion of the racemic mixture in an inert organic solvent so that the N-alkyl-D-glucamine combines preferentially with the enantiomer that forms the more insoluble diastereomeric salt, (B) precipitating and separating the resultant diastereomeric salt from the remainder of the reaction mixture, (C) decomposing the diastereomeric salt into its N-alkyl-D-glucamine and enantiomer components, and (D) isolating a substantially pure enantiomer from the resultant mixture of decomposition products.

2. The process of claim 1 wherein the aryl-substituted aliphatic carboxylic acid is a 2-arylpropionic acid.

3. The process of claim 2 wherein the 2-arylpropionic acid is 2-(6-methoxy-2-naphthyl)propionic acid, 2-(4-isobutylphenyl)propionic acid, or 2-(2-fluoro-4-biphenyl)propionic acid.

4. The process of claim 3 wherein the 2-arylpropionic acid is 2-(6-methoxy-2-naphthyl)propionic acid.

5. The process of claim 3 wherein the 2-arylpropionic acid is 2-(4-isobutylphenyl)propionic acid.

6. The process of claim 1 wherein the N-alkyl-D-glucamine is N-methyl-D-glucamine.

* * * * *